United States Patent [19]

Okazaki et al.

[11] 4,099,970
[45] Jul. 11, 1978

[54] DERIVATIVES OF 1,3,4-OXADIAZOLE AND ELECTROPHOTOGRAPHIC ELEMENTS CONTANING SAME

[75] Inventors: Mitsuo Okazaki, Tama; Akihiro Yamaguchi, Yokohama; Masaomi Sasaki, Tokyo, all of Japan

[73] Assignee: Ricoh Co., Ltd., Tokyo, Japan

[21] Appl. No.: 863,128

[22] Filed: Dec. 22, 1977

Related U.S. Application Data

[62] Division of Ser. No. 784,618, Apr. 4, 1977.

[30] Foreign Application Priority Data

Apr. 12, 1976 [JP] Japan ................................. 51-40374

[51] Int. Cl.$^2$ ..................... C07D 271/00; G03G 5/06
[52] U.S. Cl. ............................. 96/1.5 N; 260/307 G; 542/429; 542/447; 260/439 CY
[58] Field of Search ................... 260/307 G, 439 CY; 542/447, 429; 96/1.5

[56] References Cited

U.S. PATENT DOCUMENTS

| 3,189,447 | 6/1965 | Neugebauer et al. ................. 96/1.5 |
| 3,925,410 | 12/1975 | Van Landuyt et al. ... 260/439 CY X |

FOREIGN PATENT DOCUMENTS

2,117,430  10/1971  Fed. Rep. of Germany .......... 96/1.5

OTHER PUBLICATIONS

Lorkowski et al.; "Ferrocene Derivatives, VIII, Preparation of Monomeric & Polymeric Ferrocenylene Oxadiazoles," J. Prakt Chem., 35(3-4), 149-158 (1967) Ger.

*Primary Examiner*—Allen B. Curtis
*Attorney, Agent, or Firm*—Blanchard, Flynn, Thiel, Boutell & Tanis

[57] ABSTRACT

1,3,4-Oxadiazle derivatives expressed by the general formula

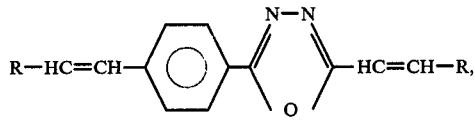

wherein R represents cyanophenyl, nitrophenyl, dialkylaminophenyl (wherein alkyl has 1 – 4 carbon atoms), julolidyl, N-alkylcarbazoyl (wherein alkyl has 1 – 4 carbon atoms) or ferrocenyl radical are photoconductive substances possessing high sensitivity and are compounds useful as a constituent of electrophotographic plates.

7 Claims, No Drawings

DERIVATIVES OF 1,3,4-OXADIAZOLE AND ELECTROPHOTOGRAPHIC ELEMENTS CONTANING SAME

This is a division of application Ser. No. 784,618, filed Apr. 4, 1977.

BACKGROUND OF THE INVENTION (a) Field of the Invention

The present invention relates to 1,3,4-oxadiazole derivatives and the use of those derivatives for electrophotographic plates.

(b) Description of the Prior Art

There have recently been developed a variety of highly sensitive electrophotographic plates comprising a combination of charge-generating materials with charge-transport materials as effective constituents. For instance, U.S. Pat. Nos. 3,791,826 and 3,837,851 describe electrophotographic plates having a photosensitive layer comprising a combination of a charge-generating layer consisting of an organic photoconductive substance with a charge-transport layer consisting of 2,4,7-trinitro-9-fluorenone or triaryl pyrazoline compound. U.S. Pat. Nos. 3,764,315 and 3,879,200 describe electrophotographic plates having a photosensitive layer formed by dispersing a charge-generating pigment in a charge-transport material.

To date, varieties of useful charge-generating materials have been proposed, but as for the charge-transport material, truly useful ones have scarcely been proposed. Besides, the art of using oxadiazole compounds as a charge-transport material is unprecedented.

SUMMARY OF THE INVENTION

The principal object of the present invention is to provide 1,3,4-oxadiazole derivatives which are excellent as charge-transport materials and can be easily manufactured.

Another object of the present invention is to provide a photoconductive composition comprising a 1,3,4-oxadiazole derivative as a charge-transport material.

The 1,3,4-oxadiazole derivatives according to the present invention are compounds expressed by the following general formula.

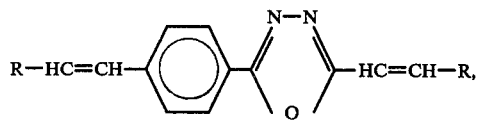

wherein R represents cyanophenyl, nitrophenyl, dialkylaminophenyl (wherein alkyl has 1 – 4 carbon atoms), julolidyl, N-alkylcarbazolyl radical (wherein alkyl has 1 – 4 carbon atoms) or ferrocenyl radical.

A compound as above can be synthesized through the following chemical reaction:

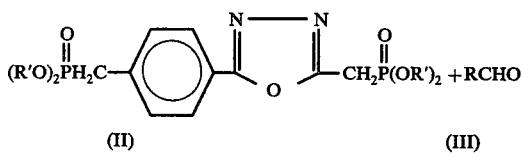

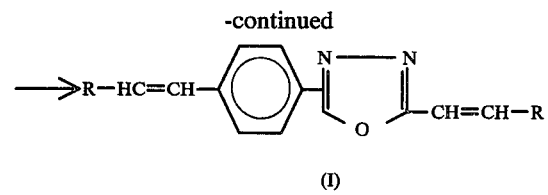

wherein R' represents an alkyl radical having 1 – 4 carbon atoms, and R represents the same as described in the foregoing.

That is to say, this compound can be obtained by effecting a reaction between 2-methyl dialkylphosphonate-5-[4'-(methyl dialkylphosphonate)phenyl]-1,3,4-oxadiazole expressed by the general formula (II) and an aldehyde expressed by the general formula (III). To be more precise, it will suffice to react a compound expressed by the general formula (II) with a compound expressed by the general formula (III) in the presence of a basic catalyst under gentle and simple conditions wherein both compounds are stirred for a short time within the reaction solvent at a temperature in the range of from room temperature to 100° C or thereabouts. In this way, the intended compound expressed by the general formula (I) in the present invention can be manufactured as a high-purity product at a high yield. As the applicable basic catalyst, the generally known basic substances such as caustic soda, caustic potash, alcoholates like sodium methylate, etc., sodium hydride and sodium amide can be cited. By virtue of the addition of such a catalyst, there can be obtained a satisfactory result. As the applicable reaction solvent, there can be cited methyl alcohol, ethyl alcohol, propyl alcohol, butyl alcohol, benzene, toluene, xylene, chlorobenzene, dioxane, N,N-dimethyl formamide, dimethyl sulfoxide, tetrahydrofuran, etc., and the reaction progresses easily within these generally known organic solvents. The starting material 2-methyl dialkylphosphonate-5-[4'-(methyl dialkylphosphonate)phenyl]-1,3,4-oxadiazole for preparing the compound expressed by the general formula (I) can be easily synthesized by heating trialkylphosphite and halomethyl compound corresponding thereto either directly or within an inert solvent such as toluene. In this context, as the alkyl for said trialkyl phosphite, such ones as, for instance, methyl, ethyl, etc. having less than 4 carbon atoms are preferable.

A compound expressed by the general formula (I) above acts effectively as a charge-transport material for electrophotographic plates.

Electrophotographic plates employing a charge-generating material combined with a charge-transport material are classified into two types. The electrophotographic plate of type-1 is one consisting of a conductive support and a photosensitive layer having a thickness of about 3 – 50μ a formed on said support, wherein the material for said photosensitive layer is prepared by dispersing a pigment as a charge-generating material in a system consisting of a charge-transport material and a binding agent.

The photoconductive support consists of a metallic plate, e.g., aluminum plate, stainless steel plate, iron plate, nickel plate, etc., or a glass plate, plastic plate or paper with a metal deposited thereon through evaporation, or a plastic plate or paper processed for conductivity by coating a conductive agent thereon.

As the applicable charge-generating material, there are various inorganic substances such as Se, SeAs, SeTe, SeTeAs, CdS and cadmium sulfoselenide disclosed in U.S. Pat. No. 3,764,315, and there are known a great number of organic pigments, such as, for instance, cyanine, phthalocyanine, disazo, indigoid, quinacridone, polynuclear quinone, bis-benzimidazole, perylene, methine, azo, xanthene and violanthrone dyes described in U.S. Pat. Nos. 3,775,105, 3,850,630, 3,870,516, 3,877,935, 3,879,200, 3,887,366, 3,894,868 and 3,904,407, Japanese Patent Publication Nos. 30332/1972 and 70538/1973, etc.

As the applicable binding agent, substances being capable of transmitting light having a wavelength sensible for said charge-generating material and having an electric resistance sufficient for holding an electric charge deposited on the surface of the photosensitive layer are useful. As substances satisfying these properties various organic high-molecular compounds are known. To cite examples of useful high-molecular compounds, there are such resins as polyamide, polyurethane, acetal resin, butylol resin, polyester, epoxide resin, alkyd resin, polyketone, polycarbonate, polyvinyl ketone, polystyrene, polyacrylamide, polyethylene, polybutadiene, polyvinyl chloride, maleic resin, acrylic resin, methacrylic resin and silicone resin, cellulose, gelatin, etc.

In order to form said photosensitive layer, it will suffice to follow the procedure that the binding agent and the 1,3,4-oxadiazole derivative are dissolved in a solvent, e.g., toluene or tetrahydrofuran, a pigment as a charge-generating material is added to the resulting solution and dispersed thoroughly therein by means of a ball-mill or the like, and the thus obtained mixture solution is coated on the aforesaid support and dried thereafter.

Said 1,3,4-oxadiazole derivative according to the present invention for use as a charge-transport material to constitute the photosensitive layer of the electrophotographic plate of type-1 is desirably contained in an amount of about 30 - 80% based on the gross weight of the photosensitive layer. And, as for the amount of the photoconductive pigment, to wit, the pigment use as the charge-generating material, application of a surprisingly small amount thereof can bring about a sensitivity well sufficient for electrophotographic process. Therefore, there is no necessity for adding the pigment as charge-generating material in a large amount, that is, the amount thereof to be applied is in the range of from less than 50% to more than 5% at the utmost based on the gross weight of the photosensitive layer.

The electrophotographic plate of type-2 employing a charge-generating material combined with a charge-transport material is one consisting of a conductive support, a first layer consisting essentially of a charge-generating material formed on said support, and a second layer comprising a charge-transport material and a binding agent formed on said first layer. As the charge-generating material and the binding agent herein, those substances described above with respect to the electrophotographic plate of type-1 are applicable.

In order to form the charge-generating layer, in the case of employing an inorganic charge-generating material which can be deposited through evaporation such as Se, SeAs, CdS, SeTe, SeTeAs, cadmium sulfoselenide, etc., it is preferable to form said layer on the support by depositing same through evaporation. In the case of employing an organic charge-generating material other than these inorganic substances, or when occasion demands, said inorganic substance, the charge-generating material is dispersed in a dispersion medium, the resulting liquid is coated on the support, and then said dispersion medium is evaporated, whereby the charge-generating layer is formed. In this case, it also will suffice to dissolve a small amount of the aforesaid binding agent in the dispersion medium beforehand. Accordingly, it is possible to make this charge-generating layer very thin, thereby realizing an appropriate thickness in the range of about 5 - 0.1$\mu$. Increase of the thickness beyond this range will not lead to any practical result. Further, this charge-generating layer can be composed of plural layers as taught in U.S. Pat. No. 3,791,826.

On the charge-generating layer there is provided a charge-transport layer consisting essentially of 1,3,4-oxadiazole derivative according to the present invention as a charge-transport material together with a binding agent. In order to form this charge-transport layer, it will do to follow the procedure that said binding agent and 1,3,4-oxadiazole derivative are dissolved in a solvent to prepare a coating solution, and said coating solution is applied onto the charge-generating layer and dried thereafter. The thickness of this charge-transport layer is desirably in the range of about 3 - 50$\mu$: increase of the thickness beyond 50$\mu$ will entail a lowering of the sensitivity while decrease of the thickness beyond 3$\mu$ will entail a lessening of the mechanical strength of the photosensitive layer.

The amount of 1,3,4-oxadiazole derivative to constitute the charge-transport layer according to the present invention is desirably in the range of about 30 - 90% based on the gross weight of the charge-transport layer.

In both electrophotographic plates of type-1 and type-2, it is possible to provide a barrier layer consisting of, for instance, aluminum oxide as taught in U.S. Pat. No. 3,791,826 by interposing same in between the photosensitive layer and the support.

DESCRIPTION OF THE PREFERRED EMBODIMENTS

Reference Example

After adding 24g of triethyl phosphite to 11.3g of 2-bromomethyl-5-(4'-bromomethylphenyl)-1,3,4-oxadiazole, the temperature of the mixture was raised gradually. At a temperature of 110° C, there began generation of ethyl bromide, and at a temperature of 140° - 150° C, the mixture was stirred for 3 hours. After cooling the reaction product down to room temperature, the unreacted portion of triethyl phosphite was removed under reduced pressure (28°-35° C/4mm Hg), whereby there were obtained 17.2g (yield 93.5%) of 2-methyl diethylphosphonate-5-(4'-methylphenyl diethylphosphonate)-1,3,4-oxadiazole (hereinafter called 'Compound A') in the form of an orange-colored oily substance as the residue.

Elementary analysis:

|  | C | H | N |
|---|---|---|---|
| calculated for $C_{18}H_{28}N_2O_7P_2$: | 48.43% | 6.33% | 6.28% |
| found: | 47.85% | 6.10% | 6.01% |

Infrared absorption spectrum (according to liquid film method) $\nu_{p=o}$ 1250 cm$^{-1}$; $\nu_{p\text{-}o\text{-}c}$ 1050, 970 cm$^{-1}$.

EXAMPLE 1

By adding a solution prepared by dissolving 0.4g (0.0174 gram atom) of metallic sodium in 15 ml of ethanol to 2.0g (0.0045 mole) of Compound A obtained in the Reference Example above and 1.7g (0.0096 mole) of p-diethyl aminobenzaldehyde, heating the resulting mixture for 2 hours while recycling, cooling it down to room temperature and thereafter diluting it with 20 ml of water, there were obtained orange-colored acicular crystals. The thus obtained crude crystals were filtered, washed in water and dried thereafter. The yield of crystals was 2.1g (yield: 95.5%), and the melting point thereof was in the range of 172.0° – 173.5° C.

When these crude crystals were recrystallized by employing benzene, there was obtained pure 2-(p-diethyl aminostyryl)-5-[4'-(p-diethyl aminostyryl)-phenyl]-1,3,4-oxadiazole having a melting point in the range of 173.0° – 174.0° C.

Elementary analysis:

|  | C | H | N |
|---|---|---|---|
| calculated for $C_{32}H_{36}N_4O$: | 78.01% | 7.37% | 11.37% |
| found: | 77.92% | 7.35% | 11.37% |

$H_5C_2$\ $\phantom{xx}$N—⬡—HC=CH—⬡—[N—N/O]—HC=CH—⬡—N$\phantom{xx}$/$C_2H_5$ (Compound No. 1)
$H_5C_2$/ $\phantom{xxxxxxxxxxxxxxxxxxxxxxxxxxxxxxxxxxxxxxxxxxxxxxxxxxxxxxxxxxxx}$\$C_2H_5$

EXAMPLE 2

By adding a solution prepared by dissolving 1.5g (0.065 gram atom) of metallic sodium in 100 ml of ethanol to 10g (0.022 mole) of Compound A and 6g (0.046 mole) of p-cyanobenzaldehyde, heating the resulting mixture for 1 hour while recycling, and cooling it down to room temperature, there were separated crystals. Then, the thus separated crystals were taken out by filtering, washed in water and dried thereafter. The yield of crystals was 8.3g (yield: 94.3%), and the melting point thereof was in the range of 308° – 310° C.

When these crude crystals were recrystallized by employing N,N-dimethyl formamide, there was obtained a citrine, acicular crystalline compound of the following composition having a melting point in the range of 309.5° – 311.0° C.

Elementary analysis:

|  | C | H | N |
|---|---|---|---|
| calculated for $C_{26}H_{16}N_4O$: | 78.98% | 4.03% | 13.99% |
| found: | 77.95% | 4.02% | 14.08% |

NC—⬡—HC=CH—⬡—[N—N/O]—HC=CH—⬡—CN (Compound No. 2)

EXAMPLE 3

2.2g (0.02 mole) of potassium tert-butoxide were slowly added to a solution prepared by dissolving 2.2g (0.005 mole) of Compound A and 2.1g (0.01 mole) of 9-julolidine aldehyde in 20 ml of N,N-dimethyl formamide. Subsequently, by stirring for 1 hour at room temperature, the resulting mixture was reacted. The thus reacted mixture was then diluted with 20 ml of water, and the reaction product was taken out in the form of crystals by filtering, washed in water, and dried thereafter. The yield of crystals was 2.6g (yield: 96.3%), and the melting point thereof was in the range of 198° – 200° C (decomposition point).

When these crude crystals were recrystallized by employing acetic acid, there was obtained an organge-colored, acicular crystalline compound of the following composition having a melting point of 200° C (decomposition point).

Elementary analysis:

|  | C | H | N |
|---|---|---|---|
| calculated for $C_{36}H_{36}N_4O$: | 79.97% | 6.71% | 10.36% |
| found: | 79.59% | 6.70% | 10.31% |

EXAMPLE 4

4.0g (0.036 mole) of potassium tert-butoxide were slowly added to a solution prepared by dissolving 4.0g (0.009 mole) of Compound A and 2.9g (0.019 mole) of p-nitrobenzaldehyde in 35 ml of N,N-dimethyl formamide. Subsequently, by stirring for 1 hour at room temperature, the resulting mixture was reacted. The thus reacted mixture was then diluted with 40 ml of water, and the reaction product was taken out in the form of crystals by filtering, washed in water, and dried thereafter. The yield of crystals was 3.8g (yield: 95.0%), and the melting point thereof was in the range of 206° – 208° C.

When these crude crystals were recrystallized by employing N,N-dimethyl formamide, there was obtained a brown-colored, acicular crystalline compound of the following composition having a melting point in the range of 207° – 208° C.
Elementary analysis:

|  | C | H | N |
|---|---|---|---|
| calculated $C_{24}H_{16}N_4O_5$: | 65.45% | 3.66% | 12.72% |
| found: | 65.25% | 3.67% | 12.65% |

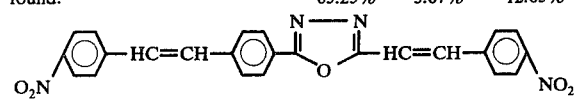

EXAMPLE 5

2.1g (0.019 mole) of potassium tert-butoxide were slowly added to a solution prepared by dissolving 2.0g (0.005 mole of Compound A and 2.1g (0.009 mole) of N-ethylcarbazole-3-aldehyde in 20 ml of N,N-dimethyl formamide. Subsequently, by stirring for 1.5 hour at room temperature, the resulting mixture was reacted. The thus reacted mixture was then diluted with 20 ml of water, and the reaction product was taken out in the form of crystals by filtering, washed in water, and dried thereafter. The yield of crystals was 2.4g (yield 92.3%), and the melting point thereof was in the range of 211° – 223.5° C.

When these crude crystals were recrystallized by employing N,N-dimethyl formamide, there was obtained a yellow-colored, acicular crystalline compound of the following composition having a melting point in the range of 222.5° – 224.5° C.
Elementary analysis:

|  | C | H | N |
|---|---|---|---|
| calculated for $C_{40}H_{32}N_4O$: | 82.16% | 5.52% | 9.58% |
| found: | 81.85% | 5.50% | 9.41% |

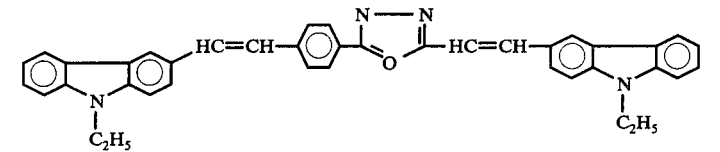

EXAMPLE 6

By adding a solution prepared by dissolving 0.3g (0.013 gram atom) of metallic sodium in 30 ml of ethanol to 2.0g (0.004 mole) of Compound A and 1.9g (0.009 mole) of ferrocenyl aldehyde, heating the resulting mixture for 40 minutes while recycling, and thereafter cooling it down to room temperature, there were separated crystals. Then, the thus separated crystals were taken out by filtering, rinsed with methanol and dried thereafter. The yield of crystals was 2.2g (yield: 87.8%), and the melting point thereof was in the range of 223.0° – 225.0° C.

When these crude crystals were recrystallized by employing n-butanol, there was obtained a red-colored, acicular crystalline compound of the following composition having a melting point in the range of 225.0° – 227.0° C.
Elementary analysis:

|  | C | H | N |
|---|---|---|---|
| calculated for $C_{32}H_{26}N_2OFe_2$: | 67.87% | 4.64% | 4.95% |
| found: | 67.90% | 4.61% | 4.93% |

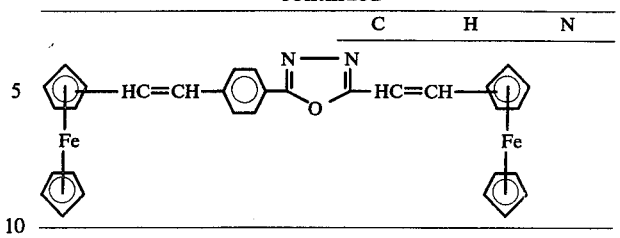

In following will be given some examples of the electrophotographic plates prepared by employing 1,3,4-oxadiazole derivatives according to the present invention a charge-transport material.

EXAMPLE 7

A liquid composition according to the following formulation was thoroughly dispersed, and then it was coated uniformly on tracing paper and dried thereafter, whereby an electrophotographic sensitive material having a 10μ-thick photosensitive layer was obtained.

| compound obtained in Example 2 (as charge-transport material) | 10g |
|---|---|
| Cu-phthalocyanine pigment (as charge-generating material) | 1g |
| polymethylacrylate | 5g |
| tetrahydrofuran | 100g |

The sensitivity of the thus prepared electrophotographic sensitive material in terms of the amount of exposure required for half decay (the amount of exposure required for reducing the initial potential imparted to the surface of a photosensitive material by negative corona discharge to half upon exposure to a tungsten lamp light) was 9.2 lux.sec.

EXAMPLE 8

By coating a tetrahydrofuran dispersion containing 2 wt.% of Dian Blue (C.I. No. 21180) having a grain size of about 1μ as prepared by crushing and dispersing within a ball-mill and drying thereafter on an aluminum plate, a charge-generating layer was formed. Meanwhile, by dissolving 225 mg of polyester resin (namely, Polyester Adhesive 49000 manufactured by Du Pont Inc., U.S.A.) in 2.5g of tetrahydrofuran and adding 225 mg of the compound obtained in Example 1 to the resulting solution, a uniform dispersion was prepared. Subsequently, this dispersion was coated on the charge-generating layer formed previously on said aluminum plate by pouring and spreading thereon, whereby a 20μ-thick charge-transport layer was formed. The sensitivity of the thus prepared electrophotographic sensitive material in terms of the amount of exposure required for half decay was 4.2 lux.sec. measured in accordance with the procedure of Example 7.

EXAMPLE 9

850 mg of tetrahydrofuran dispersion of Dian Blue used in Example 8, 1g of tetrahydrofuran solution containing 10 wt.% of Polyester Adhesive 49000 and 100 mg of the compound obtained in Example 1 were thoroughly crushed and dispersed within a ball-mill. Subsequently, the thus obtained dispersion was coated on an aluminum plate by pouring and spreading, whereby an electrophotographic sensitive material provided with a photosensitive layer having a thickness of about 20μ was prepared.

The amount of exposure required for half decay of the thus prepared photosensitive material was 3.2 lux.-sec. measured by means of the procedure of Example 7 except that the corona discharge was made positive.

EXAMPLE 10

100g of the compound obtained in Example 6, 8g of $CdS_{0.2}$—$Se_{0.8}$ having a mean grain size of 1.5μ and 100g of Polyester Adhesive 49000 as charge-generating pigment and 3l of tetrahydrofuran were thoroughly crushed and dispersed within a ball-mill. Subsequently, the thus obtained dispersion was coated on an aluminum plate by pouring and spreading, whereby an electrophotographic sensitive material was prepared. The amount of exposure required for half decay of the thus prepared photosensitive material was 1.5 lux.sec. measured in accordance with the procedure of Example 9.

EXAMPLE 11

By heating an aluminum plate at 565° C, a barrier layer of aluminum sesquioxide was formed. By depositing SeTe through evaporation on this barrier layer to the extent of 1μ in thickness, a charge-generating layer was formed. Further, by coating a solution according to the following formulation on this charge-generating layer and drying thereafter so as to form a charge-transport layer having a thickness of about 1.5μ, an electrophotographic plate was prepared.

compound obtained in Example 5 — 10g
  polyamide (Nylon 6) — 10g
  tetrahydrofuran — 100g The amount of exposure required for half decay of the thus prepared photosensitive material was 5.8 lux.-sec. measured in accordance with the procedure of Example 9.

What is claimed is:

1. A compound having the formula

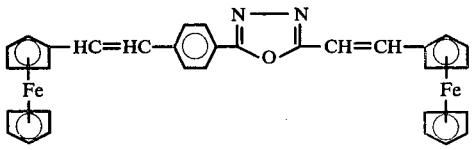

2. In an electrophotographic plate comprising a conductive support and a photosensitive layer on said support, said photosensitive layer consisting essentially of charge-generating pigment, charge-transport material and binder agent, the improvement which comprises: said charge-transport material is a compound having the formula

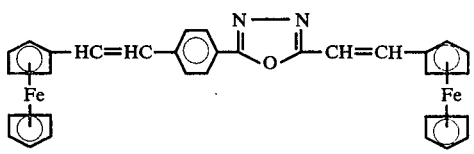

3. A plate according to claim 2, wherein said charge-generating pigment is a member selected from the group consisting of Se, SeAs, SeTe, SeTeAs, CdS, cadmium sulfoselenide, cyanine dye, phthalocyanine dye, disazo dye, indigoid dye, quinacridone dye, polynuclear quinone dye, bis-benzimidazole dye, perylene dye, methine dye and violanthrone dye.

4. In an electrophotographic plate comprising a conductive support, a charge-generating layer on said support and a charge-transport layer on said charge-generating layer, said charge-transport layer consisting essentially of a charge-transport material and binder agent, the improvement which comprises: said charge-transport material is a compound having the formula

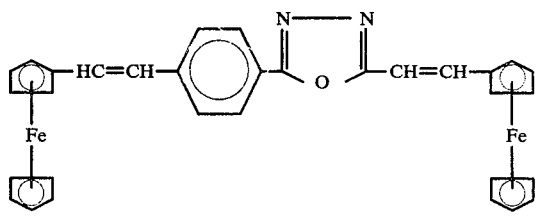

5. A plate according to claim 4, wherein said charge-generating layer comprises a member selected from the group consisting of Se, SeAs, SeTe, SeTeAs, CdS, cadmium sulfoselenide, phthalocyanine dye, disazo dye, indigoid dye, quinacridone dye, polynuclear quinone dye, bis-benzimidazoic dye, perylene dye, violanthrone dye, cyanine dye, methine dye, azo dye and xanthene dye.

6. A plate according to claim 4, wherein said charge-generating layer has a thickness of about 5 - 0.1μ, and said charge-transport layer has a thickness in the range of about 3 - 50μ.

7. A plate according to claim 4, wherein said charge-generating layer is formed by depositing through evaporation.

* * * * *